(12) United States Patent
Heise et al.

(10) Patent No.: US 9,156,859 B2
(45) Date of Patent: Oct. 13, 2015

(54) BORON CONTAINING VEGETABLE OIL BASED ANTIWEAR/ANTIFRICTION ADDITIVE AND THEIR PREPARATION

(75) Inventors: Glenn L. Heise, Britton, MI (US); Brajendra K. Sharma, Savoy, IL (US); Sevim Z. Erhan, Blue Bell, PA (US)

(73) Assignees: The United States of America, as represented by the Secretary of Agriculture, Washington, DC (US); The Penn State Research Foundation, University Park, PA (US)

( * ) Notice: Subject to any disclaimer, the term of this patent is extended or adjusted under 35 U.S.C. 154(b) by 756 days.

(21) Appl. No.: 13/241,572

(22) Filed: Sep. 23, 2011

(65) Prior Publication Data

US 2012/0083433 A1    Apr. 5, 2012

Related U.S. Application Data

(60) Provisional application No. 61/388,103, filed on Sep. 3, 2010.

(51) Int. Cl.
*C07F 5/04* (2006.01)
*C10M 139/00* (2006.01)
*C10M 159/12* (2006.01)

(52) U.S. Cl.
CPC ............. *C07F 5/04* (2013.01); *C10M 139/00* (2013.01); *C10M 159/12* (2013.01); *C10M 2207/24* (2013.01); *C10N 2230/06* (2013.01)

(58) Field of Classification Search
None
See application file for complete search history.

(56) References Cited

U.S. PATENT DOCUMENTS 3,150,157 A * 9/1964 Liao ............................ 554/77
3,256,310 A * 6/1966 Weil ............................ 558/289
3,625,899 A * 12/1971 Sawyer et al. ............. 252/75

(Continued)

OTHER PUBLICATIONS

Spelberg, J. H. L., et al., Hydrolysis and formation of Epoxidies, 2012, Wiley-VCH, Enzyme Catalysis in Organic Synthesis, 3rd Edition, edited by Drauz, K., et al., pp. 381 (4 pages).*

(Continued)

*Primary Examiner* — Yate K Cutliff
(74) *Attorney, Agent, or Firm* — John D. Fado; Howard V. Owens, Jr.

(57) ABSTRACT

Chemically-modified fatty acids prepared by reacting epoxidized fatty acids, their esters or triglyceride oils with borate compounds. The fatty acid derivatives produced are of the formula:

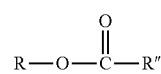

wherein R is an H, branched or straight chain alkyl or alkenyl group, aromatic-containing group, glycerol, or glyceride, R" is a C3 to C29 aliphatic chain comprising one or more of the derivatized methylene groups of the formula:

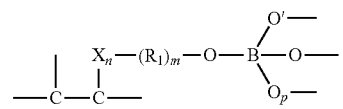

wherein
m, n, and p are independently selected from 0 and 1;
X is selected from O, NH, C(O)O, S, —C≡N, —N═C═O, —N≡C; and a borate of the formula:

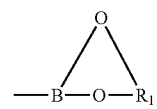

and $R_1$ is selected from aryl, and straight, branched, cyclic or heterocyclic hydrocarbons or substituted hydrocarbons. These fatty acid derivatives have utility as antiwear/antifriction additives for industrial oils, fuels, and automotive applications.

47 Claims, 9 Drawing Sheets

(56) References Cited

U.S. PATENT DOCUMENTS

| | | | | |
|---|---|---|---|---|
| 3,723,361 | A | * | 3/1973 | Newey et al. ............ 528/124 |
| 4,410,438 | A | | 10/1983 | Horodysky |
| 2009/0215657 | A1 | * | 8/2009 | Ripple ..................... 508/186 |

OTHER PUBLICATIONS

Sharma, B.K., et al., "One-Pot Synthesis of Chemically Modified Vegetable Oils", J. Agric. Food Chem., 2008, 56, pp. 3049-3056.

* cited by examiner

BORON CONTAINING VEGETABLE OIL BASED ANTIWEAR/ANTIFRICTION ADDITIVE AND THEIR PREPARATION

CROSS-REFERENCE TO RELATED APPLICATIONS

This application claims the benefit under 35 U.S.C. 1.19(e) of U.S. provisional 61/388,103 filed Sep. 30, 2010, the contents of which are incorporated by reference herein.

BACKGROUND OF THE INVENTION

1. The Field of the Invention

The invention relates to novel boron-containing fatty ester derivatives and a process for their preparation.

2. Description of the Prior Art

Antiwear/antifriction lubricants typically comprise a base oil that has been blended with any number of additives that enhance the ability of the base oil to withstand the mechanical stresses of interacting working surfaces under boundary lubrication conditions. Most of the lubricants and many of the additives currently in daily use originate from petroleum base stocks that are toxic to environment, making it increasingly difficult for safe and easy disposal. There has been an increasing demand for "green" lubricants [Rhee, I., NLGI Spokesman, 60 (5):28 (1996)] and lubricant additives in recent years due to concerns about loss of mineral oil-based lubricants to the environment and increasingly strict government regulations controlling their use.

Vegetable oils are readily biodegradable, safe to handle, environmentally friendly, non toxic fluids that are also readily renewable resources [Salunkhe, D. K. et al., World Oil Seed Chemistry, Technology and Utilization, Van Nostrand Reinhold, New York, (1992) pp. 1-8; Bockish, M. (ed.) Fats and Oils Handbook, AOCS Press, Champaign, (1998) 838]. The triacylglycerol structure of vegetable oil, which is also amphiphilic in character, give it an excellent potential as a candidate for use as a lubricant or functional fluid [Zaher, F. A. et al., Vegetable oils and lubricants, Grasas Aceites (Seville), 39:235-238 (1988); Willing, A., Chemosphere, 43:89-98 (2001)]. Triacylglycerol molecules orient themselves with the polar end at the solid surface making a close packed monomolecular [Brockway, L. O., J. Colloid Sci., 2:277-289 (1947)] or multimolecular layer [Fuks, G. I., Research in surface forces, A. B. V. Deryagin (ed.) Consultants Bureau, New York (1963) 29-88] resulting in a surface film on the material being lubricated. In addition, the vegetable oil structure provides sites for additional functionalization, offering opportunities for improving on the existing technical properties such as thermo-oxidative, low temperature stability and lubricity. These properties make them very attractive for industrial applications that have potential for environmental contact through accidental leakage, dripping, or generation of large quantities of after-use waste materials requiring costly disposal [Randles, S. J., et al., J. Syn. Lubr., 9:145-161 (1992); Dick, R. M., Process, 41:339-365 (1994)].

Limitations on the use of vegetable oil in its natural form as an industrial base fluid or as an additive relate to poor thermal/oxidation stability [Becker, R., et al., Lubr. Sc., 8:95-117 (1996); Adhvaryu, A., et al., Thermochimica Acta, 364 (1-2): 87-97 (2000) and ref. within], poor low temperature behavior [Asadauskas, S., et al., J. Am. Oil Chem. Soc., 76: 313-316 (1999); Adhvaryu, A., et al., Thermochimica Acta, 395:191-200 (2003) and ref. within], and other tribochemical degrading processes [Brophy, J. E. et al., Ann N.Y. Academy Sci., 53:836-861(1951); Miller, A. et al., Lubr. Eng., 13:553-556 (1957)] that occur under severe conditions of temperature, pressure, shear stress, metal surface and environment. To meet the increasing demands for stability during various tribochemical processes, the oil structure has to withstand extremes of temperature variations, shear degradation and maintain excellent boundary lubricating properties through strong physical and chemical adsorption with the metal. The film-forming properties of triacylglycerol molecules are believed to inhibit metal-to-metal contact and progression of pits and asperities on the metal surface. Strength of the protective fluid film and extent of adsorption on the metal surface dictate the efficiency of a lubricant's performance. It has also been observed that friction coefficient and wear rate are dependent on the adsorption energy of the lubricant [Kingsbury, E. P., ASLE Trans., 3:30-33 (1960)].

The antiwear properties of commercial additives are derived from a variety of elements capable of reacting with the metal surface and establish a stable protective film. Phosphorus, sulfur, nitrogen and zinc constitute the active element in most mineral oil based commercial antiwear additives. However, due to environmental and toxicological considerations, phosphorus may eventually be phased out from usage in the automotive industry because it has been implicated with catalyst deactivation fitted in catalytic converters [Wei, Dan-ping, Lubr. Sci., 7:365-377 (1995)].

SUMMARY OF THE INVENTION

By virtue of this invention, we now provide a novel class of chemically-modified fatty acids prepared by reacting epoxidized fatty acids or their esters with borates. In the process, an epoxidized fatty acid or an ester thereof comprising one or more oxirane rings of the formula:

is reacted with a borate compound possessing a core of the formula

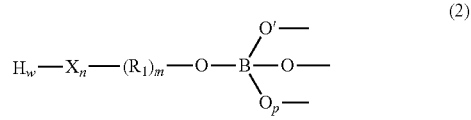

wherein m, n, p and w are independently selected from 0 and 1;
X is selected from —O— (oxy), —N(H)— (amine), —C(O)O— (carboxyl), —S— (thiol), —C≡N (cyano), —N═C═O (isocyanate), —N≡C (isocyano), and a borate of the formula:

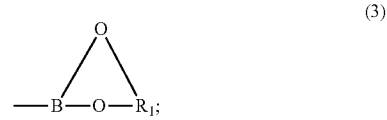

and $R_1$ is selected from aryl, and straight, branched, cyclic or heterocyclic hydrocarbons or substituted hydrocarbons. In the reaction, the oxirane ring is opened, and forms a boron-containing fatty acid derivative comprising one or more derivatized methylene groups of the formula:

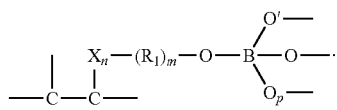

(4)

Thus, the resultant fatty acid derivatives of this invention are of the formula:

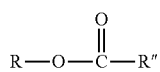

(5)

wherein R is an H, branched or straight chain alkyl or alkenyl group, aromatic-containing group, glycerol or glyceride (including O-monoglyceride or O-diglyceride), and R" is a C3 to C29 aliphatic chain comprising one or more of the above-mentioned derivatized methylene groups. The fatty acid derivatives so produced have utility as antiwear/antifriction additives for industrial oils, fuels, and automotive applications.

In accordance with this discovery, it is an object of this invention to provide novel fatty acid and triglyceride oil derivatives.

It is also an object of the invention to provide environmentally-friendly fatty acid and triglyceride oil-based industrial fluids having acceptable antiwear/antifriction performance properties.

Another object of the invention is to introduce a new use for triglyceride oils and to expand the market for an agricultural commodity.

A further object of the invention is to produce industrial fluids that reduce the demand on petroleum resources and that are biodegradable.

Yet another object of the invention is to provide a synthetic route for converting epoxidized sites of unsaturation in fatty acids and triglyceride fatty esters to borate functionalities.

Other objects and advantages of this invention will become readily apparent from the ensuing description.

DETAILED DESCRIPTION

Figure 1:
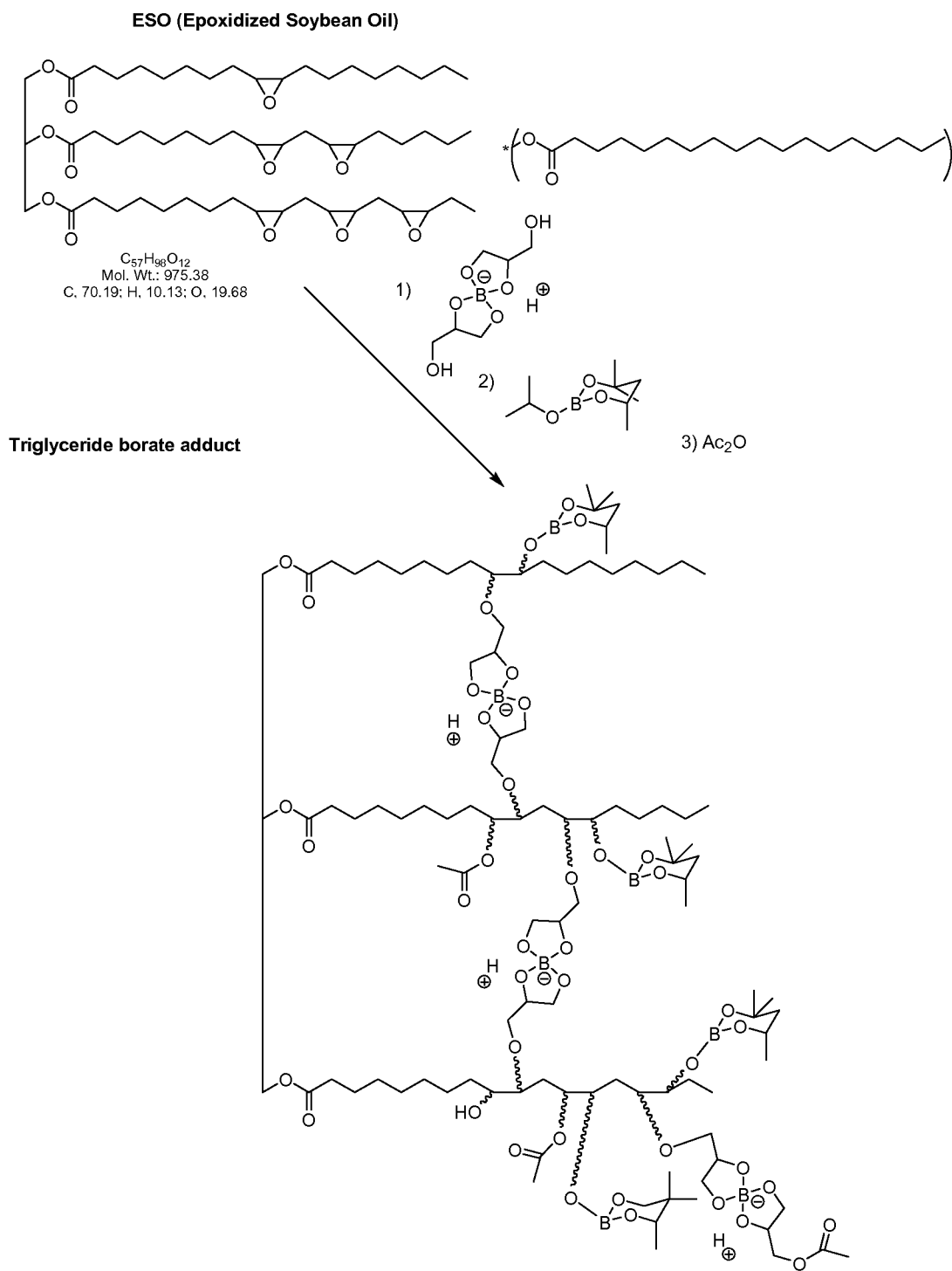
FIG. 1 shows the reaction of epoxidized soybean oil (ESO) with two borate esters, having either an alcohol or alkoxy epoxide reactive moiety. The ESO is modified via nucleophilic ring opening of the epoxide with the alcohol or alkoxy group of the borate reactants and subsequent trapping of the ring opened species with the borate esters. As shown, the boron nucleus of the first borate ester is charged and H$^+$ serves as a counter ion, while the boron nucleus of the second borate ester is uncharged. Titanium (IV) isopropoxide, Ti(OR)$_4$, serves as the Lewis acid catalyst for the reaction. Acetic anhydride, Ac$_2$O, is added as a capping reagent to cap any unreacted hydroxyl groups on the borate-derivatized product.
Figure 2:
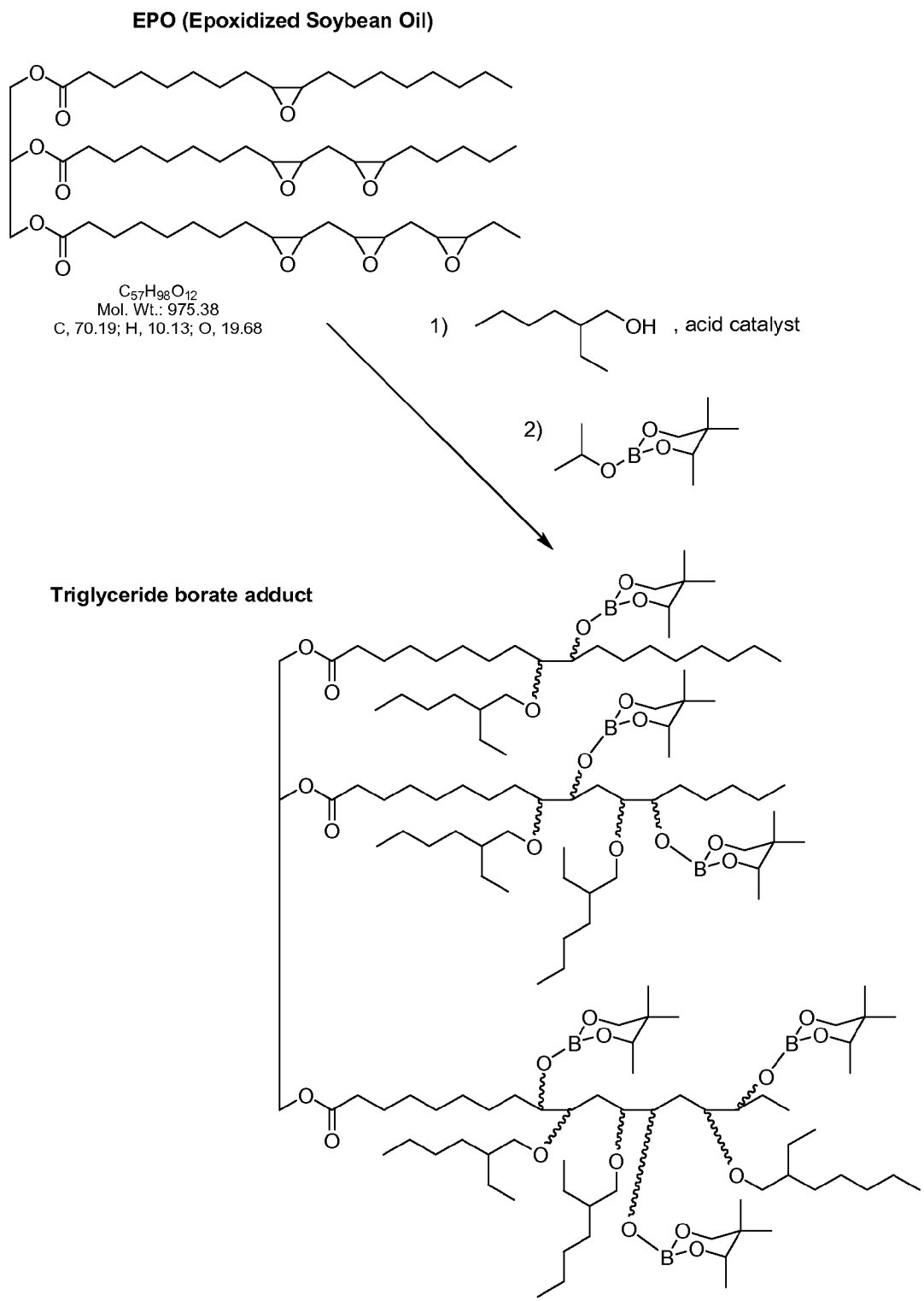
FIG. 2 shows the reaction of ESO with an organic alcohol (2-ethyl hexanol) followed by trapping of ring opened product with one of the borate esters of FIG. 1 using the same acid catalyst. The boron nucleus of the borate ester is uncharged.
Figure 3:
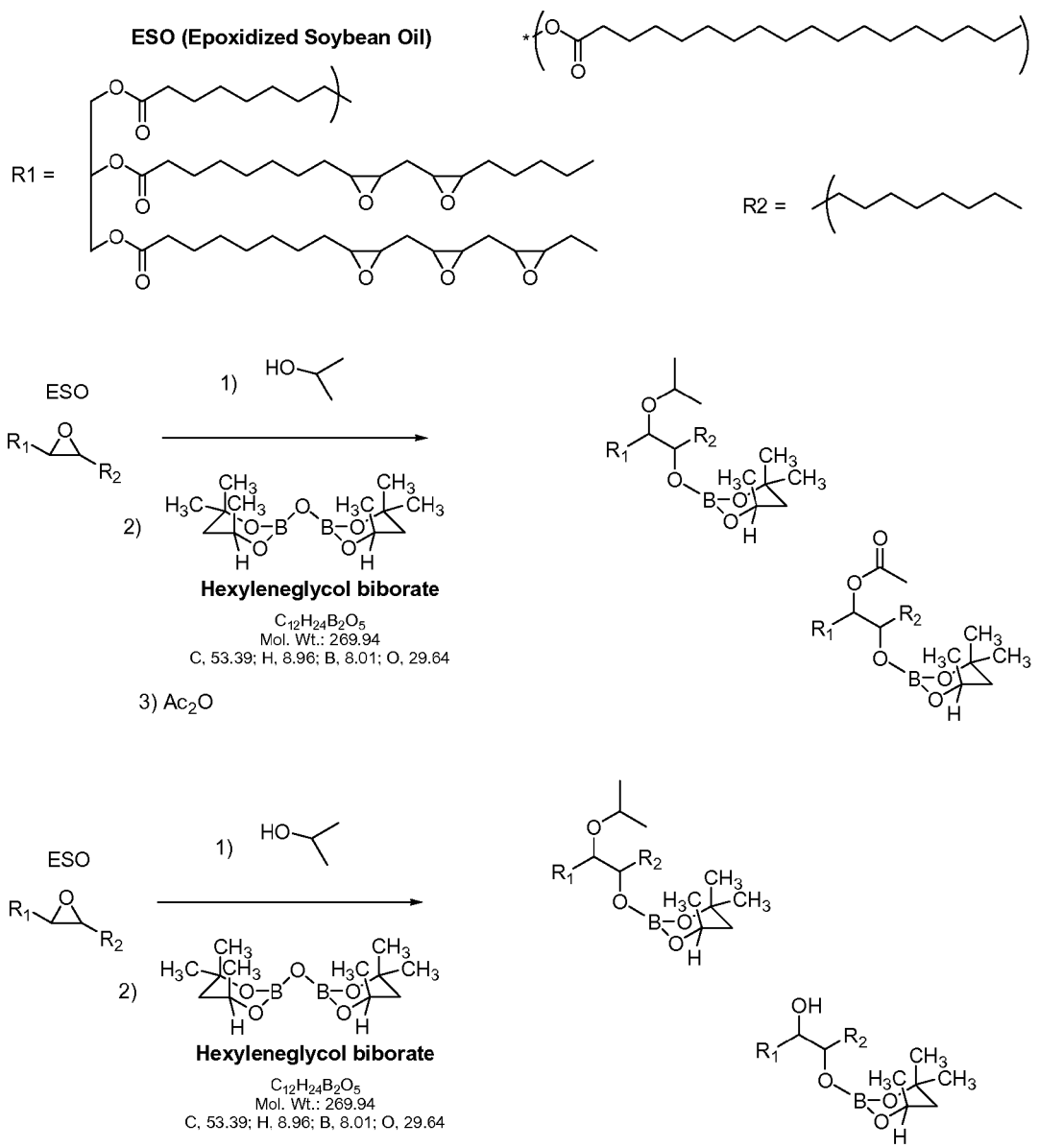
FIG. 3 shows the reaction of ESO with isopropyl alcohol followed by trapping with hexyleneglycol biborate and acetic anhydride capping reagent using the same acid catalyst as in FIG. 1. The boron nucleus of the borate ester is uncharged.
Figure 4:
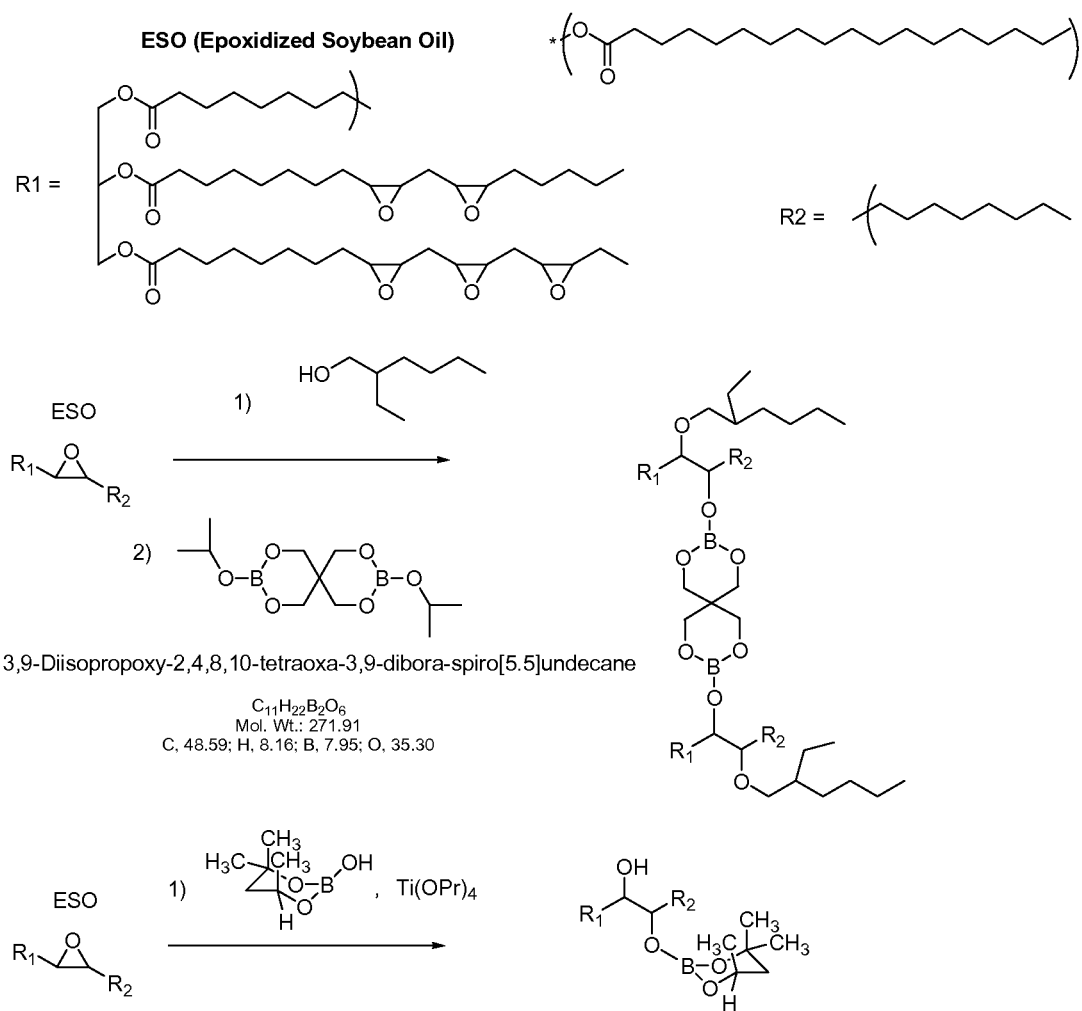
FIG. 4 shows the reaction of ESO with 3,9-diisopropoxy-2,4,8,10-tetraoxa-3,9-dibora-spiro[5,5]undecane, where the epoxy ring reacted with 2-ethyl hexanol followed by reaction with boron compound using the same acid catalyst as in FIG. 1. The boron nucleus of the borate ester is uncharged.
Figure 5:
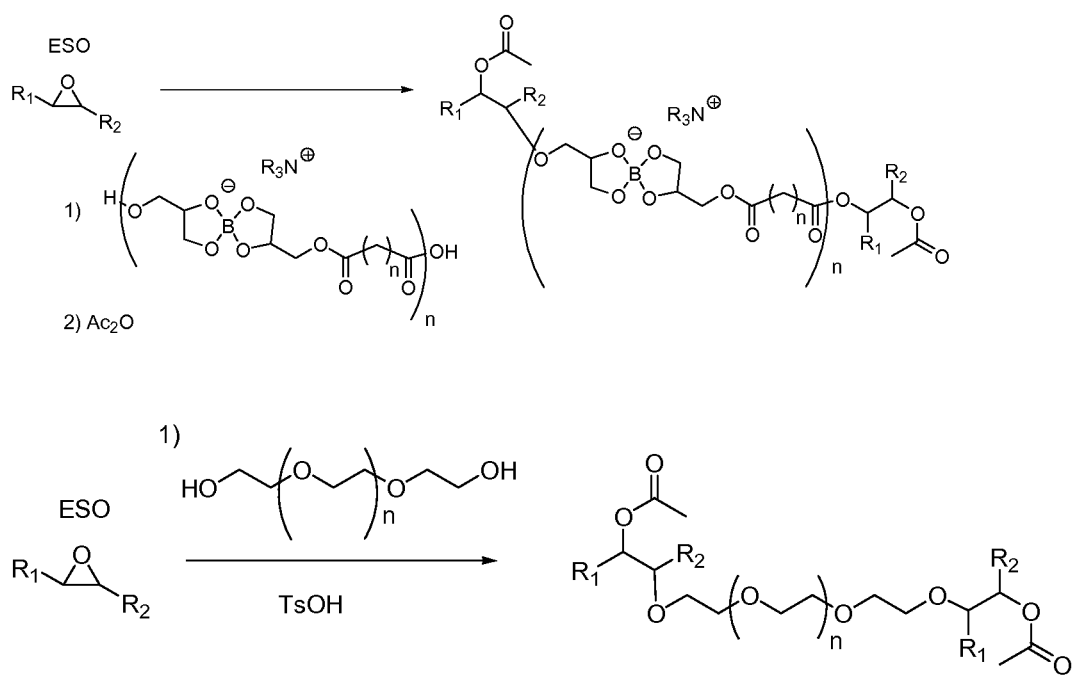
FIG. 5 shows the reaction of ESO with a borate ester having two alcohols as epoxide reactive moieties, with acetic anhydride used as a capping reagent and an acid catalyst. As shown, the boron nucleus of the borate ester is charged and an amine serves as a counter ion.

Using the process of this invention, fatty acid ester derivatives may be formed from the epoxides of a variety of unsaturated fatty acids (olefins), including vegetable oils, animal fats, or alkyl esters of vegetable oil or animal fat. These epoxides may be produced as described below or obtained from commercial sources. When preparing the epoxides, the starting unsaturated fatty acid is not critical, and any $\Delta^3$ to $\Delta^{17}$ unsaturated fatty acid (i.e. having a double bond between $\Delta^3$ and $\Delta^{17}$ inclusive) containing from 4 to 30 carbon atoms or longer may be used. Thus, starting fatty acids include fatty acids of the formula R'—COOR wherein R' is a straight or branched chain olefin, and R is H, branched or straight chain alkyl or alkenyl groups, aromatic containing groups, or glycerides (including mono-, di- or triglycerides). Preferred starting fatty acids include, but are not limited to free and esterified, unsaturated $\Delta^3$ to $\Delta^{17}$ unsaturated fatty acid containing from 4 to 22 carbon atoms, more particularly free and esterified unsaturated $\Delta^3$ to $\Delta^{17}$ unsaturated fatty acid containing from 8 to 22 carbon atoms, and most particularly free and esterified unsaturated $\Delta^9$ to $\Delta^{15}$ unsaturated fatty acid containing from 8 to 22 carbon atoms. Examples of particularly preferred unsaturated fatty acids which may be used herein include free and esterified palmitoleic acid (16:1, $\Delta^9$), oleic acid (18:1, $\Delta^9$), linoleic acid (18:2, $\Delta^{9,12}$), erucic acid (22:1, $\Delta^{13}$), and linolenic acid (18:3, $\Delta^{9,12,15}$), 5-eicosenoic acid (20:1, $\Delta^5$), 5-docosenoioc acid (22:1, $\Delta^5$), 5,13-docosadienoic acid (22:2, $\Delta^{5,13}$), petroselinic acid (16:1, $\Delta^6$), elaidic acid (18:1, $\Delta^9$), and trans isomers of any of the above.

Unsaturated fatty acids are naturally occurring in a variety of plant oils or animal fats and may be conveniently obtained for use therefrom. Without being limited thereto, oils which may be used as sources include soybean, cottonseed, corn, olive, peanut, palm, sesame, sunflower, canola, castor, safflower, linseed, grapeseed, oiticia, tung, rice, crambe, vernonia (ironweed), algae, animal fat, high erucic rape, and high oleic canola oils, with soybean oil being particularly preferred.

As starting materials to prepare the epoxides, the unsaturated fatty acids may be provided in substantially pure form or, in the alternative, they may be provided as a mixture or in impure form. Moreover, although the unsaturated fatty acids may be free acids, the reaction may also be conducted using fatty acids which are esterified with aliphatic alcohols such as methanol, ethanol, isopropanol, or branched chain alcohols such as 2-ethyl hexanol or Guerbet alcohols, or with glycerol as mono-, di- or triglycerides. However, because fatty acids occur predominantly as triglycerides in triglyceride oils, the above-mentioned naturally occurring oils are preferably used directly in the reaction, thereby foregoing the need for any preliminary fatty acid synthesis and isolation of the oil.

In a preferred embodiment wherein the fatty acids are present as triglycerides, the oils principally contemplated herein include what are normally referred to as the triglyceride drying oils. The vegetable triglyceride drying oils include plant oils and plant source-like synthetic and semi-synthetic triglycerides that can be transformed into hard, resinous materials [see Encyclopedia of Polymer Science and Technology, H. F. Monk et al., eds., John Wiley & Sons, (1966), pp. 216-234]. The expression "drying oils" is generic to both true drying oils, which dry (harden) at normal atmospheric conditions, and semidrying oils, which must be baked at elevated temperatures in order to harden. Unless otherwise indicated, "drying oil" will be used herein in its broadest sense to refer to both types of drying oil. The unsaturated fatty acids (e.g., linoleic or linolenic) residues of a drying or semidrying oil comprise double bonds that are readily available for entering into an oxidative reaction, or other reactions involved in the drying process. These oils may also include oleic fatty acid residues. Common sources of drying oils include cottonseed oil, castor oil, canola oil, linseed oil, oiticica oil, safflower oil, soybean oil, sunflower oil, corn oil, and tung oil. Of these oils, soybean oil is most readily available in both its unmodified and epoxidized state, and is therefore the most preferred. The properties of the subject industrial lubricants can be tailored by blending together different drying oils, or by blending drying oils with non-drying oils. Non-drying oils substantially comprise saturated and/or monounsaturated fatty acid residues, such as those characteristic of palmitic, stearic and oleic acid. Exemplary nondrying oils include palm, peanut, olive, and grapeseed oils.

Because of ready availability and low cost, the preferred vegetable oil use herein is soybean oil. The fatty acid constituents of soybean oil are mainly oleic (18:1), linoleic (18:2) and linolenic (18:3) acids. Though the relative distribution of fatty acids is largely dependent on the soybean type and its genetic makeup, soybean oil typically consists of approximately $C_{16}$=4%, $C_{18}$=3%, $C_{18:1}$=22%, $C_{18:2}$=66% and $C_{18:3}$=5%. The generic chemical structure of triglyceride oils for use in the invention is represented by the formula, below:

(6)

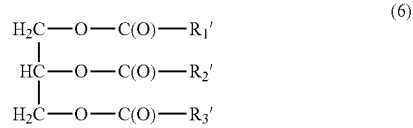

wherein $R_1'$, $R_2'$ and $R_3'$ are independently selected from C3 to C29 aliphatic fatty acid residues, that may be completely saturated or have sites of unsaturation and/or hydroxylation, provided that $R_1'$, $R_2'$ and $R_3'$ collectively have at least 1 but preferably more sites of unsaturation. In most of the common triglyceride oils listed above, the triglyceride esters are composed of C18 and C16 fatty acids, and accordingly $R_1'$, $R_2'$ and $R_3'$ are C17 or C15.

The practitioner skilled in the art will of course recognize that for fatty acid products requiring a high degree of purity or uniformity, the oils may first be hydrolyzed to obtain free fatty acids for use as starting materials in the reaction. Hydrolysis of the oils to the fatty acids may be achieved using conventional splitting techniques or alkali splitting of fats. Suitable alkali splitting techniques include, for example, treatment with sodium methoxide, or sodium or potassium hydroxide [see "A.O.C.S. Tentative Method Ca 6b-53", in: Official and Tentative Methods of the American Oil Chemist's Society, third edition, AOCS, Chicago, Ill., (1973)]. Other conventional techniques including splitting with steam under pressure are also effective.

Once the starting material has been selected, the free or esterified unsaturated fatty acids are reacted under conditions and for a period of time effective to at least partially, but preferably completely, epoxidize the carbon/carbon double bonds therein. These epoxidized fatty acids will contain one or more oxirane rings (which may also be referred to as epoxidized methylene groups):

(1)

or the equivalent formula:

(7)

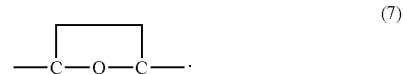

A variety of techniques for the epoxidation of olefins are known in the art and are suitable for use herein. For example, without being limited thereto, suitable techniques include those described by Qureshi et al. (Polymer Science and Technology, Vol. 17, Plenum Press, p. 250), Croco et al. (U.S. Pat. No. 5,166,372), Nowak et al. (U.S. Pat. No. 6,740,763 or 6,734,315), and preferably Bunker and Wool (Synthesis and characterization of monomers and polymers for adhesives from methyl oleate. J. Polym. Sci., Part A: Polym. Chem. 2002, 40, 451-458), the contents of each of which are incorporated by reference herein. In accordance with the preferred embodiment, epoxidation is effected by reaction of the unsaturated fatty acid with a combination of a peroxide and a carboxylic acid or its anhydride, or by reaction with a peroxycarboxylic acid such as peroxy-benzoic acid. Suitable peroxides include hydrogen peroxide or any organic peroxides which will form a peracid with a carboxylic acid or its anhydride. However, preferred epoxidation reagents include hydrogen peroxide with either formic acid, benzoic acid, acetic acid, or acetic anhydride. The order of addition is not critical, and the peroxide and carboxylic acid may be combined prior reacting with the fatty acid, or they may be added separately to the fatty acid, or all of the peroxide, carboxylic acid, and fatty acid may be combined concurrently. The reaction is preferably conducted at low temperatures, more preferably between about 0 and about 30° C., most preferably between about 0 and about 25° C. Because the reaction is exothermic, the temperature is preferably controlled such as by cooling. Temperature control is particularly preferred when reacting free, non-esterified fatty acids to prevent reaction of the acid moiety and polymerization. In a particularly preferred embodiment reaction is initiated at a temperature of approximately 0° C. and maintained at this temperature for about 1 hour, before the temperature is allowed to increase to room temperature. The reaction is typically completed in approximately 3 to 6 hours.

As an alternative to producing the epoxidized fatty acids or their esters, it is understood that many of these same epoxidized fatty acids and fatty acid esters (e.g., mono-, di- and triglycerides) may be obtained in pure form or as mixtures from commercial sources. In this embodiment, the epoxidation reaction is thereby unnecessary and the invention may proceed directly with the ring opening reaction of epoxy soybean oil with borates described herein. The final products will of course be the same.

In accordance with the process of this invention, the fatty acid epoxide produced or otherwise obtained as described above is reacted with a borate compound to form a fatty acid derivative wherein the oxirane ring (epoxide) is opened via a nucleophilic ring opening with an epoxide reactive moiety on the borate compound and subsequent trapping of the ring opened species with the borate esters. A variety of borates are suitable reactants in the reaction. By way of example and without being limited thereto, preferred borate reactants include those in FIGS. 1-9. As illustrated therein, borate reactants include but are not limited to compounds having one or more $BO_3$ and/or $BO_4$ cores, as well as heterocyclic borate cores. The borate compound will also possess an oxirane ring (epoxide) reactive moiety which reacts with one of the carbon atoms of the methylene group at the site of the opened epoxide. Epoxide reactive moieties include hydroxides, ethers, amines, carboxyls, esters, thiols, nitriles, isonitriles, and borates. Thus, the borate reactants of this invention may be shown by the general formula:

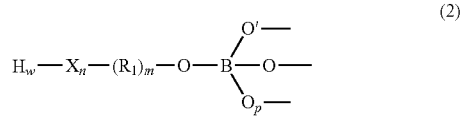

(2)

wherein:
m, n, p and w are independently selected from 0 and 1;
X is selected from —O— (oxy), —N(H)— (amine), —C(O)O— (carboxyl), —S— (thiol), —C≡N (cyano), —N=C=O (isocyanate), —N≡C (isocyano), and a borate of the formula:

(3)

and $R_1$ is selected from aryl, and straight, branched, cyclic or heterocyclic hydrocarbons or substituted hydrocarbons (i.e., any of the hydrocarbons may be optionally substituted). As represented in this formula, the $H_v$—$X_n$—$(R_1)_m$—O— portion of the borate reactant functions as an oxirane ring (epoxide) reactive moiety. For example, when n and m are 0, the epoxide reactive moiety will comprise an —OH linked directly to the B atom, while the epoxide reactive moiety may comprise an ether when n is 0 and m is 1. Further, w is 0 when X is —C≡N or —N=C=O. However, borate reactants wherein two or more of the oxygens directly linked to the boron are joined in a heterocylic ring exhibit increased stability (a reduced capacity to cross-link with other epoxides) and are preferred. The borate reactant may be charged or uncharged, as shown in the Figures, and the borate nucleus is typically negatively charged in compounds comprising four oxygens linked to each boron. When using charged borate reactants, a variety of nucleophiles or counter ions may be added therewith, including but not limited to $H^+$, $Li^+$ (e.g., alkyl or other hydrocarbons linked to lithium), and $R_4N^+$ (amines). As will be shown in greater detail hereinbelow, the particular nucleophile selected may affect the derivatized methylene group in the product.

The reaction of the epoxide of fatty acid/ester/glyceride thereof with the borate compound is conducted in the presence of an effective amount of a catalyst. Suitable catalysts should be capable of opening the oxirane ring of the epoxide, and a variety of catalysts may be used, including ionic liquids, mineral acids, Lewis acids, acidic metal oxides, acidic resins, and enzymes, with ionic liquids, mineral acids, Lewis acids or acidic metal oxides being preferred, and titanium isopropoxide, titanium ethoxide, and titanium butoxide being particularly preferred. Non-aqueous catalysts are preferred to maintain product stability. By way of example and without being limited thereto, other suitable catalysts include $H_2SO_4$, $H_3PO_4$, $BF_3$ etherate, $CeCl_3$, $ZnCl_2$, $InCl_3$, $SbCl_3$, $AlCl_3$, $Zn(ClO_4)_2$, $Cu(ClO_4)_2$, choline chloride/urea, acidic resins such as AMBERLYST-15 (Rohm Haas), and enzymes such as lipases. The amount of the catalyst may vary somewhat with the particular catalyst selected, although even very small amounts are effective. Without being limited thereto, typically the catalyst will be added at a concentration of about 0.5 mole % or higher, preferably at a concentration of about 1 to 10 mole %, and most preferably at a concentration of about 1 mole %. Although the use of a solvent is optional, the reaction is preferably conducted in the presence of a non-aqueous solvent to facilitate mixing and removal of any by-products. Organic solvents such as heptanes, hexane, toluene or other hydrocarbons, or acetone may be used. The reaction pH is not critical, although when reacting epoxidized glycerides, extremely acidic or basic conditions should be avoided to minimize their saponification. The reaction temperature is not critical, and the reaction is typically conducted at a temperature below about 160° C., preferably between about 60 to 140° C. Reaction time may vary with temperature and catalyst concentration, and the reaction typically reaches completion in less than about 2 hours at 105° C. with 5 mole % catalyst, and about 8-24 hours at 60° C. At the completion of the reaction, the catalyst may be recovered and recycled and the solvents may be removed and recovered by distillation. Because some boron-containing fatty acid derivatives may be subject to decomposition when stored for extended periods in the presence of moisture, the recovered products are preferably stored in an inert atmosphere in the absence of moisture.

The reaction of the epoxidized fatty acid or its ester with the borate reactant occurs in a single step, with the oxirane ring opening, and forming a boron-containing fatty acid derivative comprising one or more derivatized methylene groups of the formula:

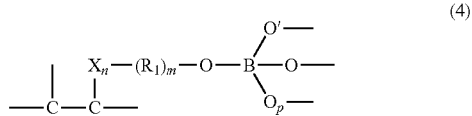
(4)

wherein n, m, p, X and $R_1$ are the same as described above. Thus, if the epoxidized fatty acid or ester is represented by the formula:

(8)

wherein R is an H, branched or straight chain alkyl or alkenyl group, aromatic containing group, glycerol, or glyceride (including O-monoglyceride or O-diglyceride), and R' is a C3 to C29 aliphatic chain hydrocarbon comprising one or more of the oxirane rings, the resultant boron containing fatty acid derivative formed is:

(5)

wherein R" is a C3 to C29 aliphatic chain hydrocarbon comprising one or more of the above-mentioned derivatized methylene groups.

Figure 6:
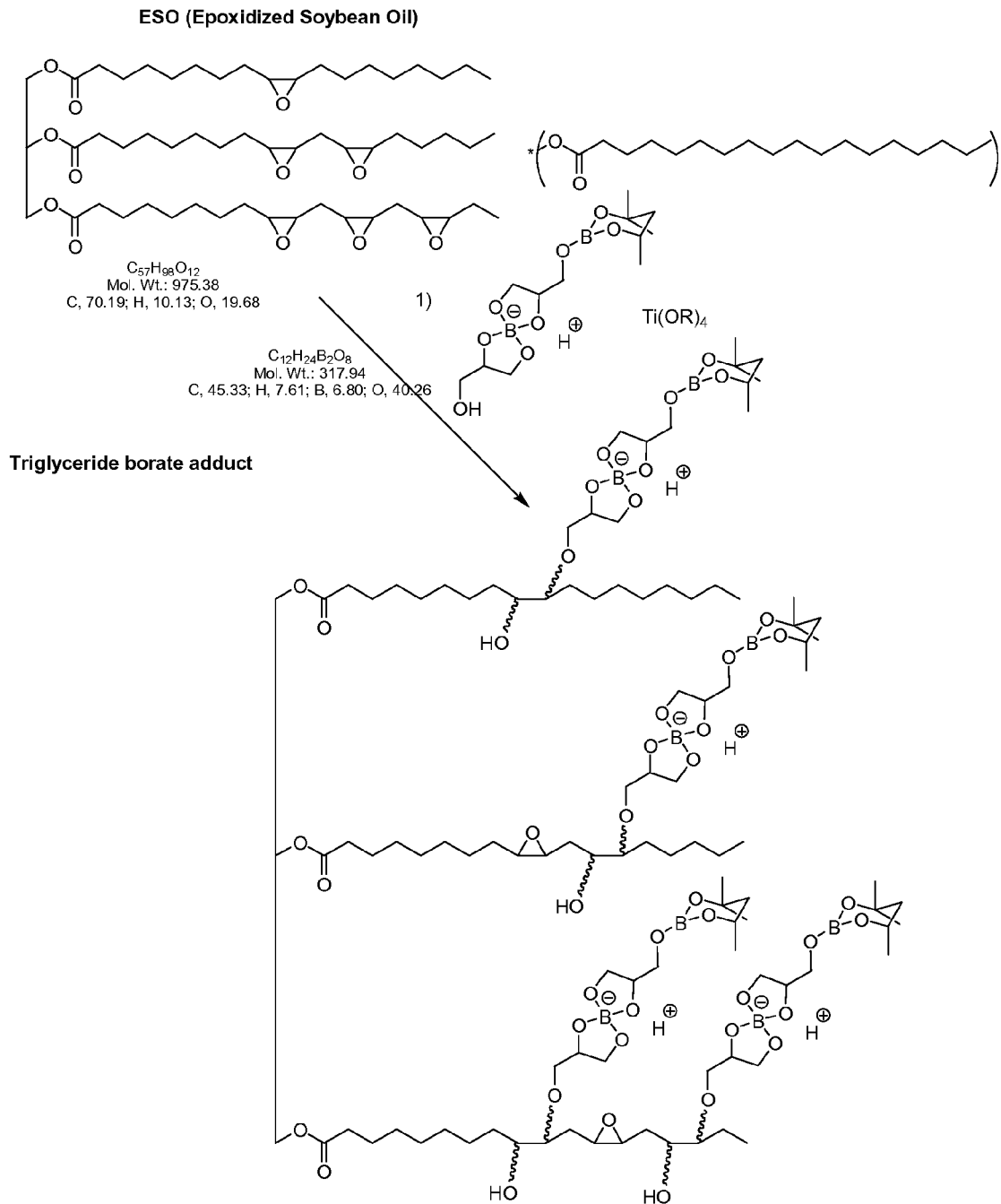
FIG. 6 shows the reaction of ESO with a borate ester having a single alcoholic as epoxide reactive moiety, using the same acid catalyst as in FIG. 1, but without a capping reagent. As shown, the boron nucleus of the borate ester is charged and H$^+$ serves as a counter ion.
Figure 7:
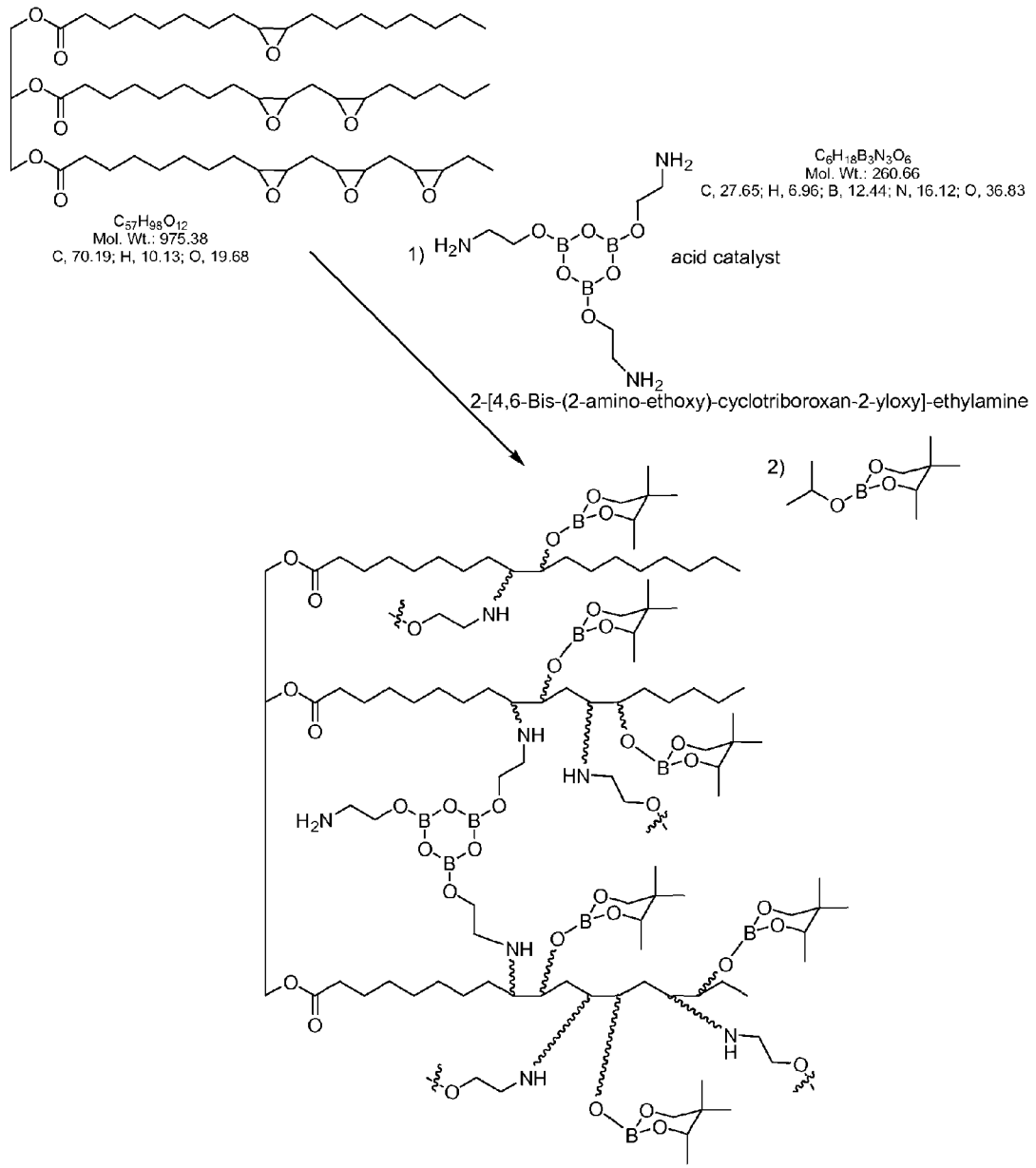
FIG. 7 shows the reaction of epoxidized soybean oil (ESO) with 2-[4,6-bis-(2-amino-ethoxy)-cyclotriboroxan-2-yloxy]-ethylamine (having amine as epoxide reactive moieties) and one of the borate esters of FIG. 1, using an acid catalyst. The boron nucleus of each of the borate esters is uncharged.
Figure 8:
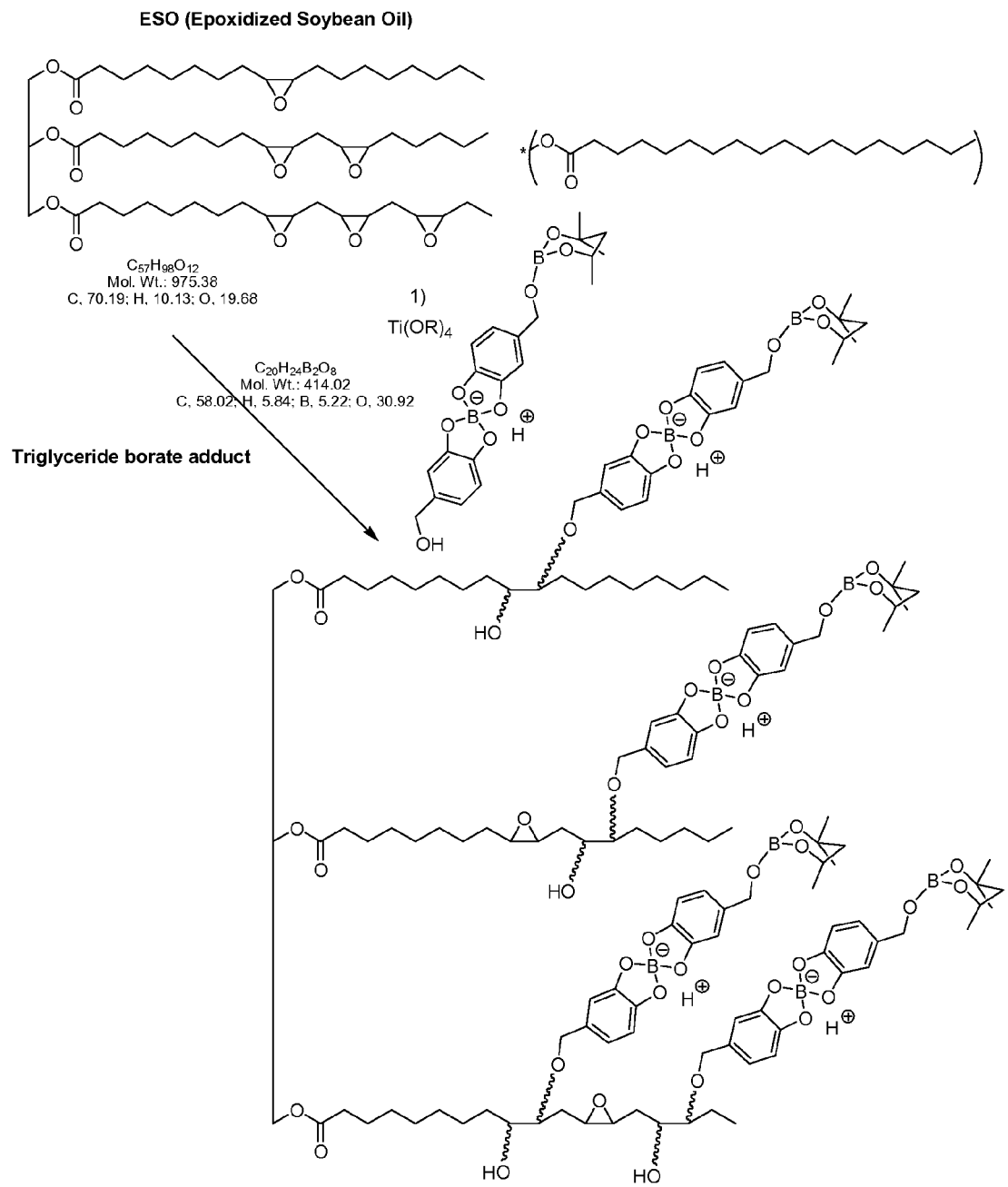
FIG. 8 shows the reaction of ESO with a borate ester having a single alcoholic epoxide reactive moiety, using the same acid catalyst as in FIG. 1, but without a capping reagent. As shown, the boron nucleus of the borate ester is charged and H$^+$ serves as a counter ion.
Figure 9:
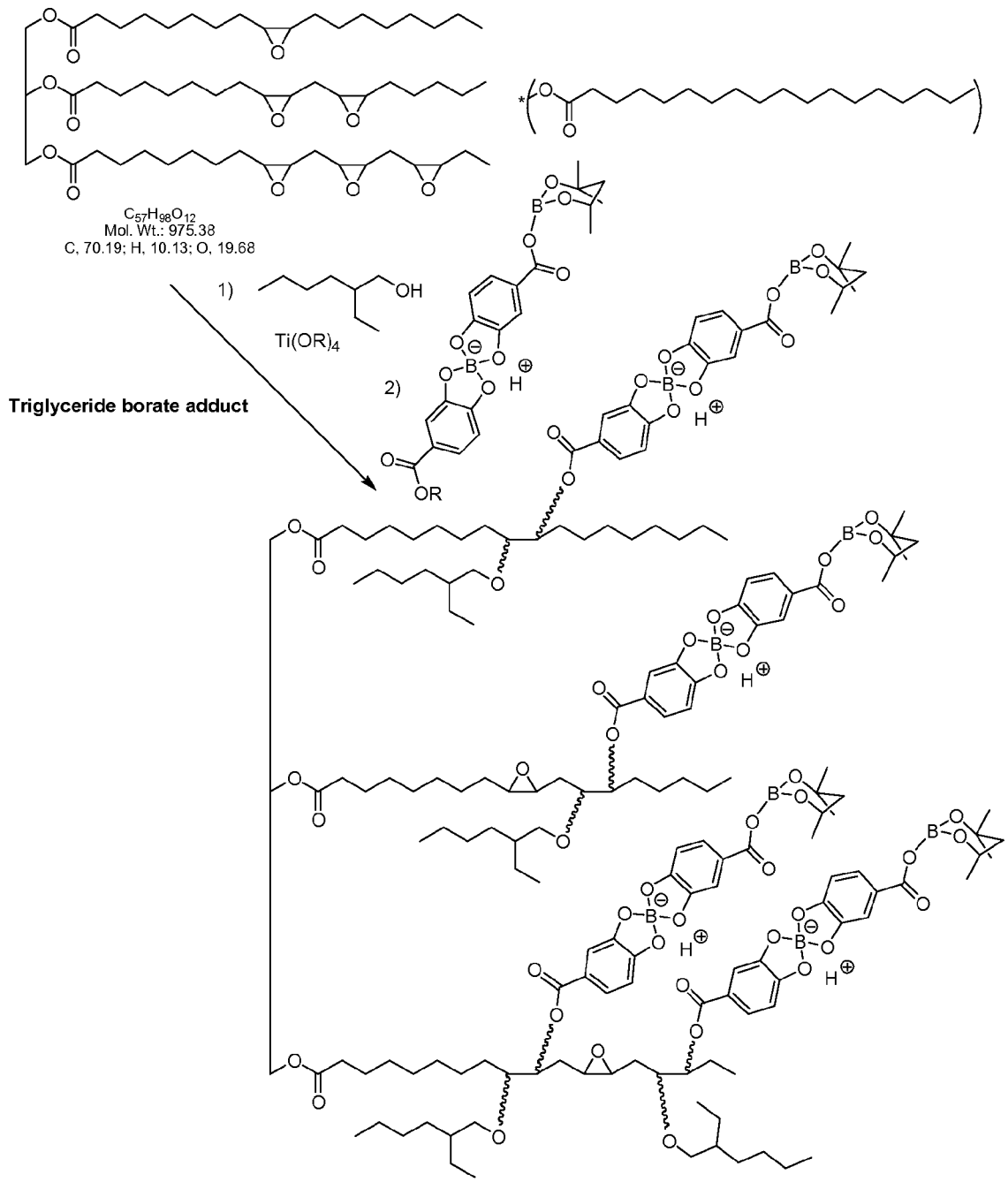
FIG. 9 shows the reaction of ESO with 2-ethyl hexanol followed by trapping with a borate ester having a single carboxylic group as epoxide reactive moiety, using the same acid catalyst as in FIG. 1. As shown, the boron nucleus of the borate ester is charged and H$^+$ serves as a counter ion.

In the product of formula (4) above, the remaining carbon of the methylene group formed from the epoxide (the leftmost C as illustrated in the formula) will typically form an hydroxide (such as shown in FIGS. 6 and 8) or react with another borate molecule (such as shown in FIGS. 1 and 7). Thus, in this embodiment, the derivatized methylene group produced is of the formula:

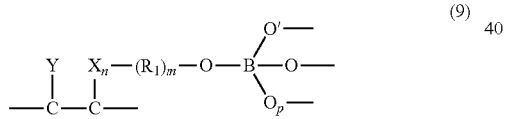
(9)

wherein
Y is —OH or a borate of the formula:

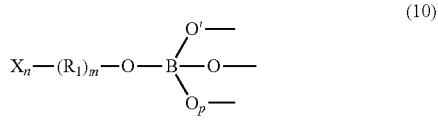
(10)

and m, n, p, X, and $R_1$ is independently as described above (with X bonded to the C of the methylene group). In the example shown in FIGS. 1 and 7, Y is of the formula:

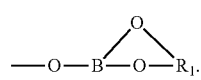
(10a)

When reacting fatty acid epoxides in triglyceride (formula 4 above), diglyceride or monoglyceride form, the resulting compounds may be characterized by formulas:

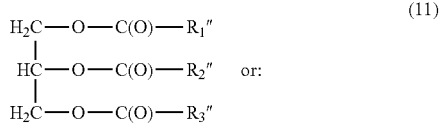
(11)

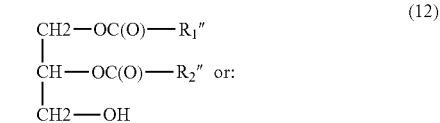
(12)

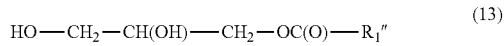
(13)

respectively, wherein $R_1''$, $R_2''$ and $R_3''$ are independently selected from C3 to C29 aliphatic fatty acid residues comprising one or more of the derivatized methylene groups of formula (4) described above.

In a first preferred optional embodiment, the borate reactant comprises two of the above-mentioned epoxide reactive moieties, such as shown in FIGS. 1, 4, 5, and 7, providing for cross-linking between two fatty acids (which may be in the same or different glycerides). In this embodiment, the borate compound of formula (2) may be shown by the formula:

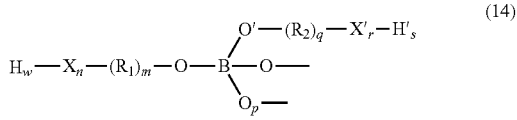
(14)

and reacts with two epoxidized fatty acids or esters thereof (the X' reacts with an oxirane ring on a second epoxidized fatty acid or an ester thereof) to form a boron-containing fatty acid derivative of the formula:

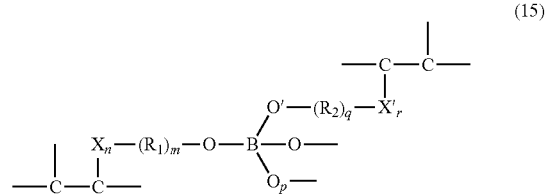
(15)

between (crosslinking) each of the two fatty acids or esters thereof. As with X in the first epoxide reactive moiety, X' is also independently selected from —O—, —N(H)—, —C(O)O—, —S—, —C≡N, —N═C═O, —N═C, and a borate of the formula:

(3)

and $R_2$ is selected from aryl, and straight, branched, cyclic or heterocyclic hydrocarbons or substituted hydrocarbons (any of the hydrocarbons may be optionally substituted).

In a second preferred optional embodiment, two or more of the oxygens directly linked to the boron in the borate reactant of formula (2) are joined in a heterocylic ring, such as shown in FIGS. 1-6, 8, and 9. As noted above, these reactants exhibit increased stability (a reduced capacity to cross-link with other epoxides). Thus, in this embodiment, the borate compound of formula (2) may be shown by any of the formulas:

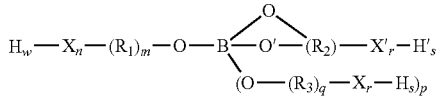 (16)

or

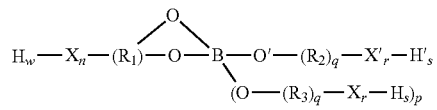 (17)

or

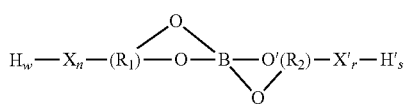 (18)

wherein q, r, and s are independently selected from of 0 and 1; X and X' are as described above; and $R_2$ and $R_3$ are independently selected from aryl, and straight, branched, cyclic or heterocyclic hydrocarbons or substituted hydrocarbons (any of which hydrocarbons may be optionally substituted). The resultant derivatized methylene groups which are formed are of the formulas:

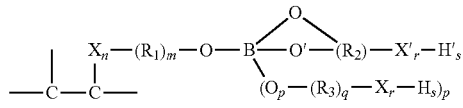 (19)

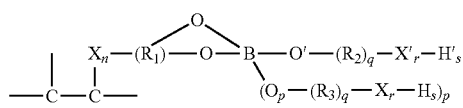 (20)

or

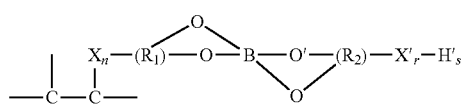 (21)

respectively.

In an alternative embodiment, it is also recognized that the oxygens directly linked to the boron in the borate reactant of formula (2) need not be joined in a heterocyclic ring. In this embodiment, the borate compound of formula (2) may be shown by the formula:

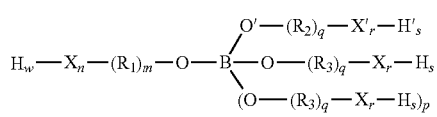 (22)

and forms derivatized methylene groups of the formula:

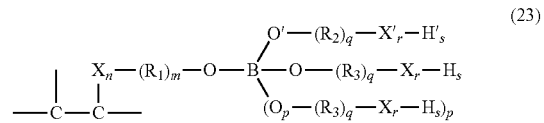 (23)

wherein q, r, s, X', $R_2$ and $R_3$ are as described above.

As described and shown in formula (9) above, one carbon of the methylene group formed from the epoxide will typically form an hydroxide ("Y" in the formula). However, in accordance with alternative preferred embodiments, the boron containing fatty acid derivatives produced may be further reacted with a "capping" reagent which is effective to react with free hydroxyls on the derivatized methylene groups. These capped products generally exhibit improved solubility and stability. These capping reactions are preferably conducted following completion of the reaction between the epoxidized fatty acid or an ester thereof and the borate reactant. A variety of capping reagents are suitable for use herein and include, but are not limited to, alcohols, anhydrides, and organic silicon hydroxides, with anhydrides such as acetic anhydride ($Ac_2O$) and alcohols such as 2-ethyl hexanol or isopropyl alcohol being particularly preferred, such as shown in FIGS. 1-5 and 9. For example, when adding a capping reagent selected from alcohols, $R_4$—OH, or anhydrides, $R_4$—C(O)—O—C(O)—$R_4$, the resultant derivatized methylene groups are of the formula:

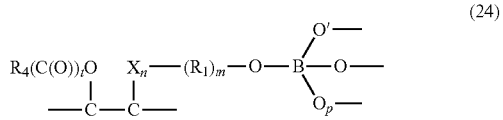 (24)

wherein t is 0 or 1 (t=0 when capping with $R_4$—OH and t=1 when capping with an anhydride); and $R_4$ is selected from the group consisting of aryl, and straight, branched, cyclic or heterocyclic hydrocarbons or substituted hydrocarbons (any of the hydrocarbons may be optionally substituted). Alternatively, when adding an organic silicon hydroxide capping reagent of the formula $Si(OR_5)_u(R_5)_v$OH, the resultant derivatized methylene groups are of the formula:

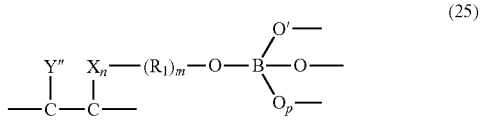 (25)

wherein Y" is a silicon derivative of the formula $Si(OR_5)_u(R_5)_vO$—, u and v are integers between 0 and 3 such that the sum of u plus v is 3, and $R_5$ is selected from aryl and straight, branched, cyclic or heterocyclic hydrocarbons or substituted hydrocarbons (again, any of the hydrocarbons may be optionally substituted).

As noted above, when using charged borate reactants different nucleophiles or counter ions may be used, and the particular nucleophile selected may affect the derivatized methylene group in the product. For instance, when using $H^+$ as the nucleophile and without addition of an above-mentioned "capping" reagent, the derivatized methylene group may comprise a hydroxy borate ester such as shown in formula (9) (with Y as —OH) and in FIGS. 6 and 8. However, when using Li+ as the nucleophile (such as provided by addition of a hydrocarbon linked to lithium), the hydrocarbon moiety may become linked to the derivatized methylene group. Thus, when the reaction is conducted in the presence of a lithium hydrocarbon nucleophile of the formula LiR$_5$, the derivatized methylene groups formed are of the formula:

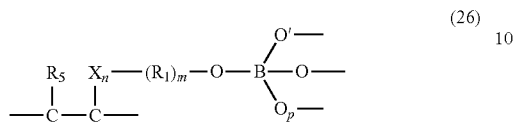
(26)

wherein R$_5$ is selected from aryl and straight, branched, cyclic or heterocyclic hydrocarbons or substituted hydrocarbons (any of the hydrocarbons may be optionally substituted).

In accordance with another alternative embodiment, the reaction of the epoxidized fatty acid or an ester thereof with the borate compound may be conducted in the presence of a halogen acid. In this embodiment, the halogen may become linked to the derivatized methylene group. Thus, if the halogen acid is of the formula HY', the derivatized methylene groups formed are of the formula:

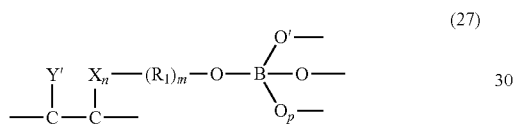
(27)

wherein Y' is the halogen.

The boron-containing fatty acid derivatives of this invention have superior properties which render them useful as additives to base stocks for biodegradable lubricant applications, such as crankcase oils, transmission fluids, two-cycle engine oils, marine engine oils, greases, hydraulic fluids, drilling fluids, metal cutting oils, and the like. Base stocks useful in the lubricant formulations contemplated by the invention are typically high molecular weight hydrocarbons, and may be of mineral, vegetable, or synthetic origin, or mixtures thereof. Exemplary base oils are described in Erickson et al. (U.S. Pat. No. 5,023,312, the contents of which are incorporated herein by reference). Of course, the objectives of the invention to maximize the biodegradability of the lubricant system would be achieved with a vegetable oil base stock. In an alternative embodiment, the boron-containing fatty acid derivatives may also be used as an additive to hydrocarbon-based fuels such as gasoline, jet fuel or diesel fuel, to improve their anti-wear properties.

Though formulations of base stocks with the boron-containing fatty acid derivatives of the invention meet or exceed many, if not all, specifications for lubricant end-use applications, it is contemplated that other additives may be used in conjunction with the boron-containing fatty acid derivatives in order to enhance the properties of the base stock. Illustrative of these additives are detergents, antiwear agents, antioxidants, viscosity index adjusters, pour point depressants, corrosion protectors, friction coefficient modifiers, colorants and the like as well-known in the art.

The amount of boron-containing fatty acid derivatives additive formulated with a base oil will of course depend upon the end-use application of the formulation. For most of the end-uses indicated above, the concentration of additive will be in the range of about 1-12% (w/w), typically at least about 4% (w/w), and preferably in the range of about 5-8% (w/w).

The following examples are intended only to further illustrate the invention and are not intended to limit the scope of the invention as defined by the claims.

EXAMPLE 1

Epoxidized soybean oil was reacted with a variety of charged and uncharged borate esters. Reactions were conducted with titanium (IV) isopropoxide catalyst, with and without Ac$_2$O capping reagents. The reactions and products are shown in FIGS. 1-9.

It is understood that the foregoing detailed description is given merely by way of illustration and that modifications and variations may be made therein without departing from the spirit and scope of the invention.

We claim:

1. A method of making boron-containing fatty acid derivatives comprising reacting an epoxidized fatty acid or an ester thereof comprising one or more oxirane rings of the formula:

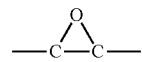

with a borate compound comprising a core of the formula:

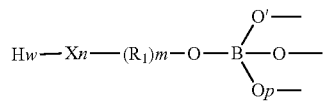

to open said oxirane ring and form a boron-containing fatty acid derivative comprising one or more derivatized methylene groups of the formula:

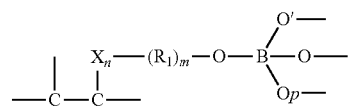

wherein m, n, p and w are independently selected from the group consisting of 0 and 1;

X is selected from the group consisting of —O—, —N(H)—, —C(O)O—, —S—, —C≡N, —N═C═O, —N═C, and a borate of the formula:

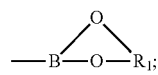

and

R$_1$ is selected from the group consisting of aryl, and straight, branched, cyclic or heterocyclic hydrocarbons or substituted hydrocarbons.

2. The method of claim 1 wherein said borate compound is of the formula:

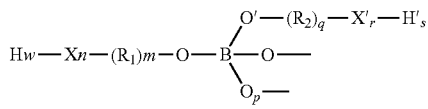

and reacts with two of said epoxidized fatty acids or esters thereof such that said X' reacts with an oxirane ring on a second epoxidized fatty acid or an ester thereof and forms boron-containing fatty acid derivatives of the formula:

between each of said two fatty acids or esters thereof, wherein q, r, and s are independently selected from the group consisting of 0 and 1;

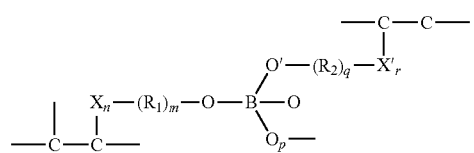

X' is selected from the group consisting of —O—, —N(H)—, —C(O)O—, —S—, —C=N, —N=C=O, —N=C, and a borate of the formula:

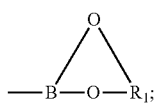

and $R_2$ is selected from the group consisting of aryl, and straight, branched, cyclic or heterocyclic hydrocarbons or substituted hydrocarbons.

3. The method of claim 2 wherein said epoxidized fatty acid or an ester thereof comprises an epoxidized glyceride molecule and said two fatty acids or esters thereof are on a single glyceride molecule.

4. The method of claim 2 wherein said epoxidized fatty acid or an ester thereof comprises epoxidized glyceride molecules and said two fatty acids or esters thereof are on different glyceride molecules.

5. The method of claim 1 wherein said borate compound comprises the formula:

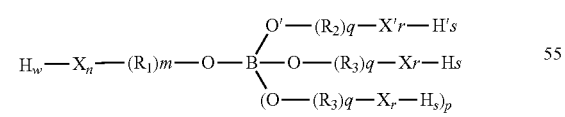

and forms derivatized methylene groups of the formula:

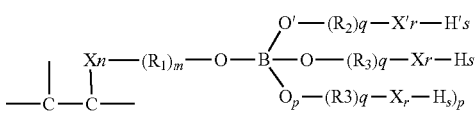

wherein q, r, and s are independently selected from the group consisting of 0 and 1;

X' is selected from the group consisting of —O—, —N(H)—, —C(O)O—, —S—, —C=N, —N=C=O, —N=C, and a borate of the formula:

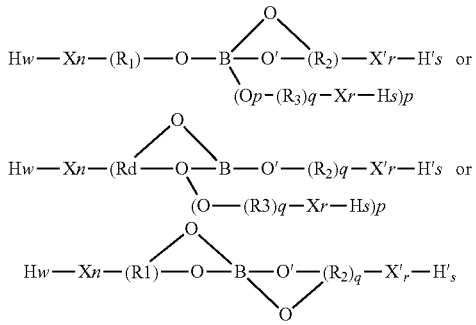

and

R2 and R3 are independently selected from the group consisting of aryl, and straight, branched, cyclic or heterocyclic hydrocarbons or substituted hydrocarbons.

6. The method of claim 1 wherein said borate compound is of the formula:

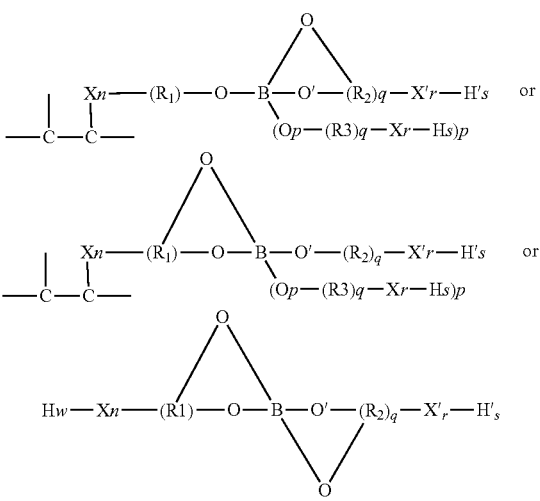

or and forms derivatized methylene groups of the formula:

respectively, wherein q, r, and s are independently selected from the group consisting of 0 and 1;

X' is selected from the group consisting of —O—, —N(H)—, —C(O)O—, —S—, —C=N, —N=C=O, —N=C, and a borate of the formula:

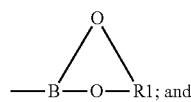

R2 and R3 are independently selected from the group consisting of aryl, and straight, branched, cyclic or heterocyclic hydrocarbons or substituted hydrocarbons.

7. The method of claim 1 wherein said epoxidized fatty acid or ester thereof is of the formula:

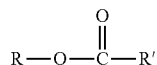

wherein R is an H, branched or straight chain alkyl or alkenyl group, aromatic containing group, glycerol, or glyceride, R' is a C3 to C29 aliphatic chain comprising one or more of said oxirane rings, and said boron-containing fatty acid derivative is of the formula:

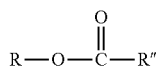

wherein said R" is a C3 to C29 aliphatic chain comprising one or more of said derivatized methylene groups.

8. The method of claim 7 wherein said R' and R" are a C7 to C21 aliphatic chain.

9. The method of claim 7 wherein said R' and R" are a C16 to C18 aliphatic chain.

10. The method of claim 1 wherein said epoxidized fatty acid or an ester thereof is selected from the group consisting of a triglyceride, diglyceride, monoglyceride, alkyl ester of triglyceride, fatty acid, fatty acid ester, and mixtures thereof.

11. The method of claim 10 wherein said epoxidized fatty acid or an ester thereof comprises an epoxidized triglyceride.

12. The method of claim 1 wherein said epoxidized fatty acid or an ester thereof comprises epoxidized triglyceride oil.

13. The method of claim 12 wherein said triglyceride oil selected from the group consisting of soybean, cottonseed, corn, olive, peanut, palm, sesame, sunflower, canola, castor, safflower, linseed, grapeseed, oiticia, tung, rice, crambe, rape, vernonia, algae, and animal fat.

14. The method of claim 1 wherein said reacting of an epoxidized fatty acid or an ester thereof with said borate compound is conducted in the presence of a catalyst effective for opening said oxirane ring.

15. The method of claim 14 wherein said catalyst is selected from the group consisting of an ionic liquid, a mineral acid, a Lewis acid, an acidic metal oxide, an acidic resin, and an enzyme.

16. The method of claim 14 wherein said catalyst comprises an ionic liquid, a mineral acid, Lewis acid or an acidic metal oxide.

17. The method of claim 14 wherein said catalyst is selected from the group consisting of titanium isopropoxide, titanium ethoxide, titanium butoxide, $H_2SO_4$, $H_3PO_4$, $BF_3$ etherate, $CeCl_3$, $ZnCl_2$, $InCl_3$, $SBCl_3$, $AlCl_3$, $Zn(ClO_4)_2$, $Cu(ClO_4)_2$, and choline chloride/urea.

18. The method of claim 1 wherein reacting of an epoxidized fatty acid or an ester thereof with said borate compound is conducted in the presence of a solvent.

19. The method of claim 1 wherein said derivatized methylene groups are of the formula:

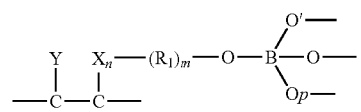

wherein
Y is —OH or a borate of the formula:

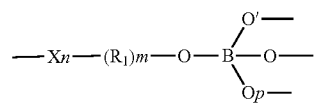

and
m, n, and p are independently selected from the group consisting of 0 and 1;
X is selected from the group consisting of —O—, —N(H)—, —C(O)O—, —S—, —C=N, —N=C=O, —N=C, and a borate of the formula:

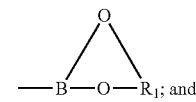

$R_1$ is selected from the group consisting of aryl, and straight, branched, cyclic or heterocyclic hydrocarbons or substituted hydrocarbons.

20. The method of claim 1 further comprising adding a hydroxide capping reagent selected from the group consisting of R4-OH and R4-C(O)—)—C(O)—R4 effective to react with intermediate free hydroxyl groups which form on said derivatized methylene groups such that said derivatized methylene groups are of the formula:

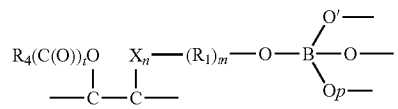

wherein
t is 0 or 1; and
R4 is selected from the group consisting of aryl, and straight, branched, cyclic or heterocyclic hydrocarbons or substituted hydrocarbons.

21. The method of claim 1 wherein said reacting is conducted in the presence of a halogen acid of the formula HY', wherein Y' is a halogen, and said derivatized methylene groups are of the formula:

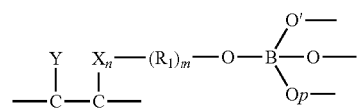

wherein Y' is a halogen.

22. The method of claim 1 wherein said reacting is conducted in the presence of a lithium hydrocarbon nucleophile of the formula LiRs, and said derivatized methylene groups are of the formula:

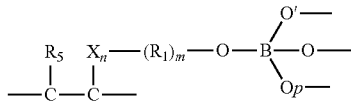

wherein R5 is selected from the group consisting of aryl and straight, branched, cyclic or heterocyclic hydrocarbons or substituted hydrocarbons.

23. The method of claim 1 further comprising adding a hydroxide capping reagent of the formula Si(ORs)u(Rs)vO-Heffective to react with intermediate free hydroxyl groups which form on said derivatized methylene groups such that said derivatized methylene groups are of the formula:

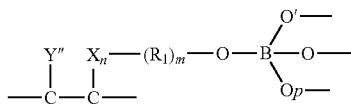

wherein

Y" is a silicon derivative of the formula Si(ORs)u(Rs)vO— wherein u and v are integers between 0 and 3 such that the sum of u plus v is 3, and Rs is selected from the group consisting of aryl and straight, branched, cyclic or heterocyclic hydrocarbons or substituted hydrocarbons.

24. A compound of the formula:

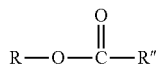

wherein said R is an H, branched or straight chain alkyl or alkenyl group, aromatic-containing group, glycerol, or glyceride, said R" is a C3 to C29 aliphatic chain comprising one or more derivatized methylene groups of the formula:

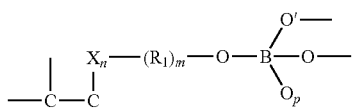

wherein m, n, and p are independently selected from the group consisting of 0 and 1;

X is selected from the group consisting of O, NH, C(O)O, S, —C≡N, —N═C═O, and —N═C; and R1 is selected from the group consisting of aryl, and straight, branched, cyclic or heterocyclic hydrocarbons or substituted hydrocarbons.

25. The compound of claim 24 said derivatized methylene group is crosslinked to a methylene group of a second C3 to C29 aliphatic chain and is of the formula:

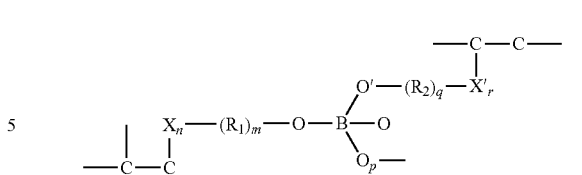

further wherein q, r are independently selected from the group consisting of 0 and 1;

X' is selected from the group consisting of O, NH, C(O)O, S, —C≡N, —N═C═O, and —N═C;

R2 is selected from the group consisting of aryl, and straight, branched, cyclic or heterocyclic hydrocarbons or substituted hydrocarbons.

26. The compound of claim 25 wherein said R comprises a glyceride, and said second aliphatic chain is esterified thereto.

27. The compound of claim 25 wherein said R comprises a glyceride, and said second aliphatic chain is esterified to a different glyceride molecules.

28. The compound of claim 24 wherein said derivatized methylene groups are of the formula:

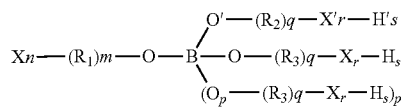

wherein q, r, and s are independently selected from the group consisting of 0 and 1;

X' is selected from the group consisting of O, NH, C(O)O, S, —C≡N, —N═C═O, and —N═C; and R2 and R3 are independently selected from the group consisting of aryl, and straight, branched, cyclic or heterocyclic hydrocarbons or substituted hydrocarbons.

29. The compound of claim 24 wherein said derivatized methylene groups are selected from the group consisting of the formulas:

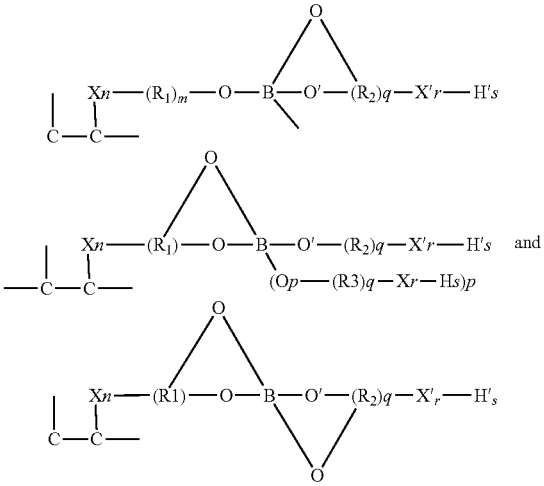

wherein q, r, and s are independently selected from the group consisting of 0 and 1;

X' is selected from the group consisting of O, NH, C(O)O, S, —C≡N, —N═C═O, and —N═C; and R2 and R3 are independently selected from the group consisting of aryl, and straight, branched, cyclic or heterocyclic hydrocarbons or substituted hydrocarbons.

30. The compound of claim 24 wherein said R and R" are a C7 to C21 aliphatic chain.

31. The compound of claim 24 wherein said R' and R" are a C16 to C18 aliphatic chain.

32. The compound of claim 24 wherein said R is selected from the group consisting of a diglyceride, alkyl esters of a diglyceride, monoglyceride, alkyl esters of a monoglyceride, and mixtures thereof.

33. The compound of claim 32 wherein said R is a diglyceride or alkyl ester of a diglyceride.

34. The compound of claim 24 wherein said derivatized methylene groups are of the formula:

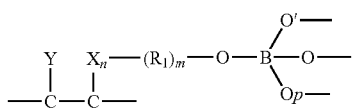

wherein

Y is selected from the group consisting of —OH, —Rs, —ORs, RsC(O)O—, a halogen, a borate of the formula:

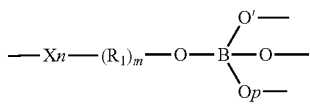

and a silicon derivative of the formula $Si(OR_5)u(R_5)vO—$ wherein u and v are integers between 0 and 3 such that the sum of u plus v is 3, and $R_5$ is independently selected from the group consisting of aryl and straight, branched, cyclic or heterocyclic hydrocarbons or substituted hydrocarbons.

35. The compound of claim 24 wherein said derivatized methylene groups are of the formula:

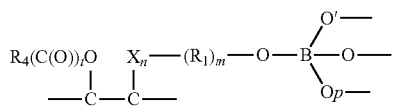

wherein t is 0 or 1; and $R_4$ is selected from the group consisting of aryl, and straight, ranched, cyclic or heterocyclic hydrocarbons or substituted hydrocarbons.

36. A composition comprising a base stock material of mineral, vegetable, animal or synthetic origin, or mixtures thereof, and a component of the formula:

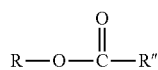

wherein said R is an H, branched or straight chain alkyl or alkenyl group, aromatic containing group, glycerol, or glyceride, said R" is a C3 to C29 aliphatic chain comprising one or more derivatized methylene groups of the formula:

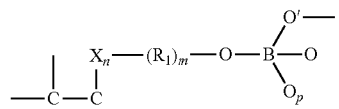

wherein m, n, and p are independently selected from the group consisting of 0 and 1;

X is selected from the group consisting of O, NH, C(O)O, S, —C≡N, —N═C═O, and —N═C; and $R_1$ is selected from the group consisting of aryl, and straight, branched, cyclic or heterocyclic hydrocarbons or substituted hydrocarbons.

37. The composition of claim 36 said derivatized methylene group is crosslinked to a methylene group of a second C3 to C29 aliphatic chain and is of the formula:

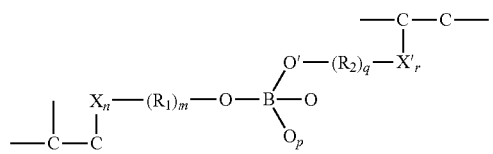

further wherein q, r, are independently selected from the group consisting of 0 and 1;

X' is selected from the group consisting of O, NH, C(O)O, S, —C≡N, —N═C═O, and —N═C; and $R_2$ is selected from the group consisting of aryl, and straight, branched, cyclic or heterocyclic hydrocarbons or substituted hydrocarbons.

38. The composition of claim 37 wherein said R comprises a glyceride, and said second aliphatic chain is esterified thereto.

39. The composition of claim 37 wherein said R comprises a glyceride, and said second aliphatic chain is esterified to a different glyceride molecules.

40. The composition of claim 36 wherein said derivatized methylene groups are of the formula:

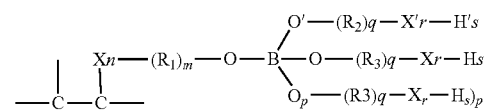

wherein q, r, and s are independently selected from the group consisting of 0 and 1;

X' is selected from the group consisting of O, NH, C(O)O, S, —C≡N, —N═C═O, —N═C; and R2 and R3 are independently selected from the group consisting of aryl, and straight, branched, cyclic or heterocyclic hydrocarbons or substituted hydrocarbons.

41. The composition of claim 36 wherein said derivatized methylene groups are selected from the group consisting of the formulas:

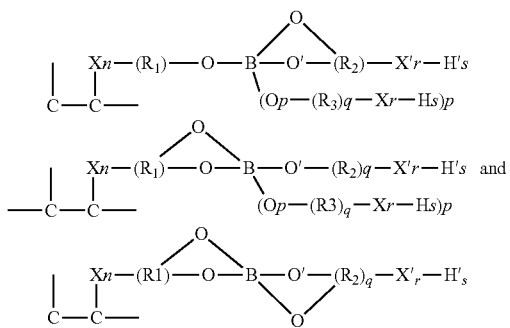

wherein
- q, r, and s are independently selected from the group consisting of 0 and 1;
- X' is selected from the group consisting of O, NH, C(O)O, S, —C=N, —N=C=O, and —N=C; and
- R2 and R3 are independently selected from the group consisting of aryl, and straight, branched, cyclic or heterocyclic hydrocarbons or substituted hydrocarbons.

42. The composition of claim 36 wherein said R and R" are a C7 to C21 aliphatic chain.

43. The composition of claim 36 wherein said R and R" are a C16 to C18 aliphatic chain.

44. The composition of claim 36 wherein said R is selected from the group consisting of a diglyceride, alkyl esters of a diglyceride, monoglyceride, alkyl esters of a monoglyceride, and mixtures thereof.

45. The composition of claim 44 wherein said R is a diglyceride or alkyl ester of a diglyceride.

46. The composition of claim 36 wherein said derivatized methylene groups are of the formula:

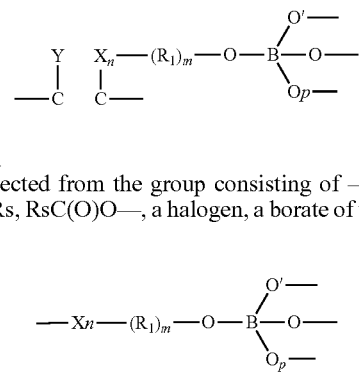

wherein
Y is selected from the group consisting of —OH, —Rs, —ORs, RsC(O)O—, a halogen, a borate of the formula:

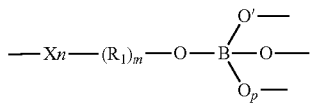

and a silicon derivative of the formula Si(ORs)u(Rs)vO— wherein u and v are integers between 0 and 3 such that the sum of u plus v is 3, and Rs is independently selected from the group consisting of aryl and straight, branched, cyclic or heterocyclic hydrocarbons or substituted hydrocarbons.

47. The composition of claim 36 wherein said derivatized methylene groups are of the formula:

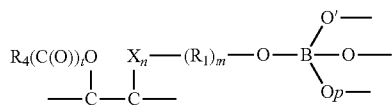

wherein
t is 0 or 1; and
$R_4$ is selected from the group consisting of aryl, and straight, branched, cyclic or heterocyclic hydrocarbons or substituted hydrocarbons.

* * * * *